United States Patent [19]

Schiek

[11] Patent Number: 4,707,131
[45] Date of Patent: Nov. 17, 1987

[54] OPTICAL ARRANGEMENT FOR PHOTOMETRICAL ANALYSIS MEASURING DEVICES

[76] Inventor: Oswald Schiek, 3, Fritz-Reuter-Strasse, 6900 Jena, District of Gera, German Democratic Rep.

[21] Appl. No.: 786,994

[22] Filed: Oct. 15, 1985

[30] Foreign Application Priority Data

Nov. 1, 1984 [DD] German Democratic Rep. ... 268965
Mar. 1, 1985 [DD] German Democratic Rep. ... 273669

[51] Int. Cl.$^4$ ............................................. G01N 21/17
[52] U.S. Cl. ...................................... 356/73; 356/338; 250/574
[58] Field of Search ................. 356/73, 218, 337, 338, 356/339; 250/574

[56] References Cited

U.S. PATENT DOCUMENTS 4,027,973 6/1977 Kaye ..................................... 356/73

Primary Examiner—Eugene R. LaRoche
Assistant Examiner—Robert J. Pascal

[57] ABSTRACT

An optical arrangement in photometrical measuring devices for use in fluorescence and absorption measurements, extinction, nephelometrical and turbidimetrical measurements comprises a light source for emitting a monochromatic radiation, a field aperture for said radiation, and lenses which focus said monochromatic radiation onto a sample material for being analyzed. The sample, in response to said monochromatic radiation emits a first radiation portion incorporating the measuring informations from said sample, and a second radiation portion not containing measuring information. An optical imaging system is provided for directing said first radiation portion onto a detector. A removable optical member for retaining the second radiation portion is provided adjacent the optical imaging system and has an aperture greater than the field aperture.

10 Claims, 4 Drawing Figures

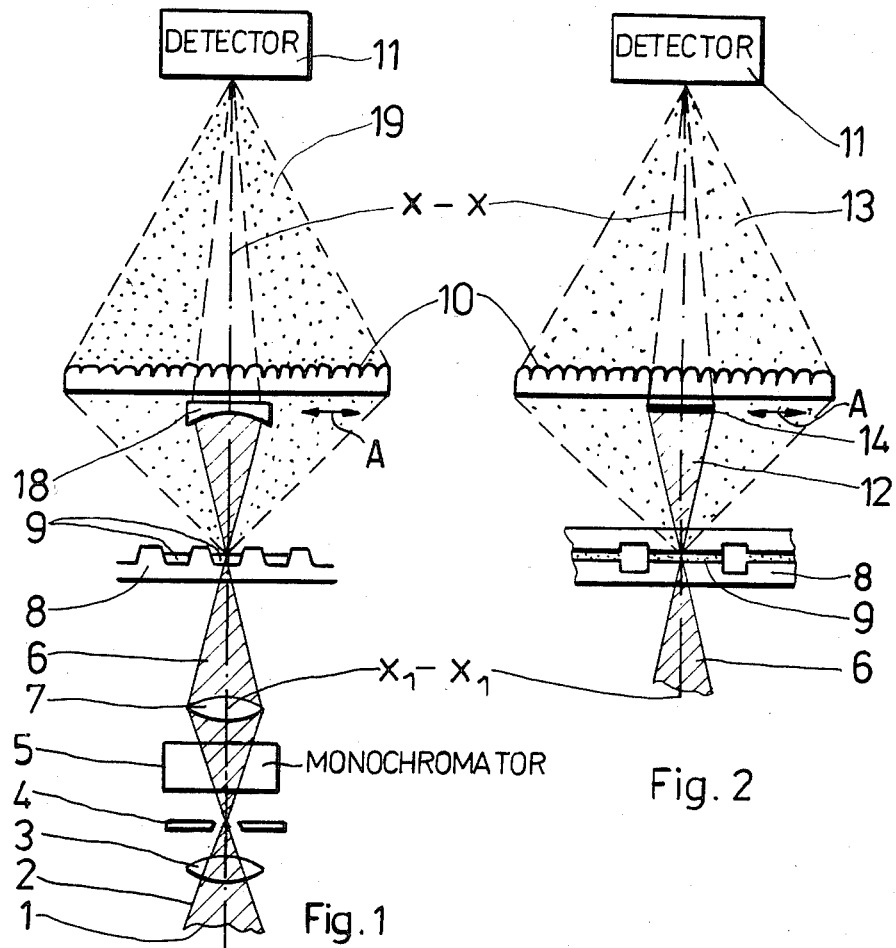
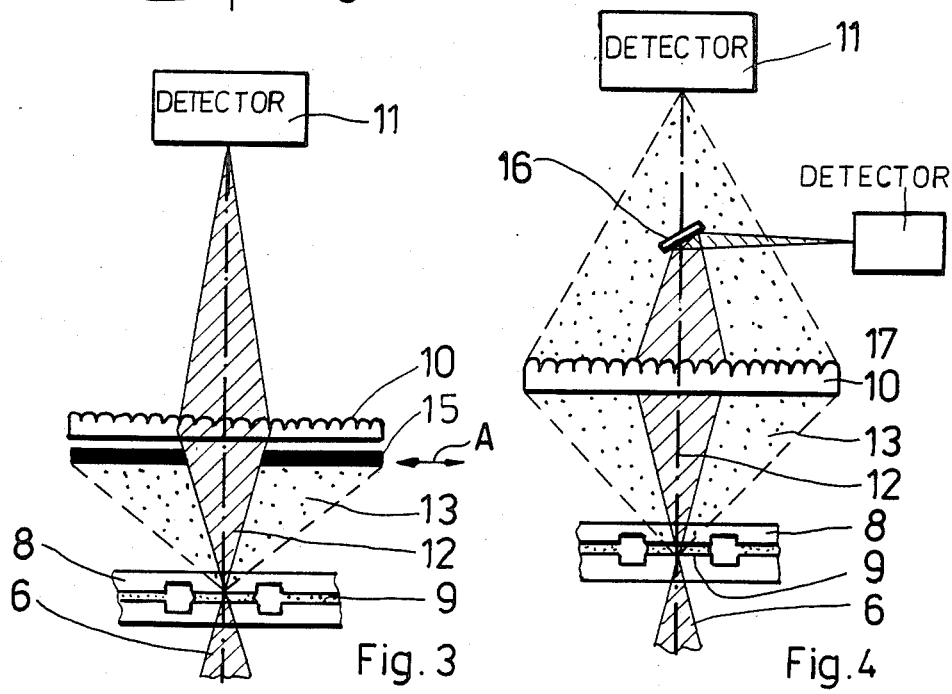

OPTICAL ARRANGEMENT FOR PHOTOMETRICAL ANALYSIS MEASURING DEVICES

BACKGROUND OF THE INVENTION

The invention relates to an optical arrangement for photometrical analysis measuring devices, particularly for use in fluorescence and absorption measurements, for extinction, nephelometrical and turbidimetrical measurements.

In fluorometric measurements a sample material to be analyzed is excited by a primary radiation to emit a fluorescence radiation.

It is a condition to capture the fluorescence radiation at the widest possible angle which has to be achieved by suitable measures.

It is a further condition that the fluorescence radiation subject to measurement is not superimposed on portions of the excitation radiation. The geometry of the radiation paths is in accordance with one of the three following known arrangements.

Firstly, it is known that the exciting radiation and the fluorescence radiation propagate along axes which have the same direction. After having excited a sample material to fluoresce the exciting radiation is retained by blocking filters.

In a second known kind of arrangement, the axis of excitation radiation and the direction of the fluorescence radiation which is exploited for measurement include an angle with one another.

In a third kind of arrangement, the fluorescence light which is subject to measurement is back-radiated at a definite angle of inclination relative to the excitation radiation into the space lying in front of the entry window of the cell containing the sample material.

For better suppression of the excitation light, arrangements in accordance with the second and third type are preferably used. When an arrangement of the first type is employed, particular demands on the blocking filter have to be made. Since the intensity of the excitation radiation is a multiple of the fluorescence radiation intensity the filter has to be capable of entirely absorbing the excitation radiation and of a high transmissivity for the fluorescence radiation, apart from being free of an intrinsic fluorescence.

Since these conditions very often cannot be matched to one another optimally, this first type arrangement involves radiation output losses. Therefore the requirement of performing absorption measurements and fluorescence measurements while persuing a given path for the radiation can only be satisfied with a reduced output in the case of fluorescence measurements.

The degree of turbidity of a substance very often serves to determine the concentration of the light scattering particles which cause the turbidity. The turbidity measurement, as a rule, is carried out turbidimetrically or nephelometrically.

In the first case, the effective extinction of the turbid solution is measured in which the light losses of the measuring bundle of light, when passing the substance, are caused rather by light scattering than by absorption. In the case of nephelometric measurement the intensity of the scattered light is directly measured and used, for example, for determining the concentration values. The known optical arrangements for both measuring systems distinguish from one another in that the optical axes of the light concentrating systems coincide in front of and subsequently to the cuvette in measuring devices adapted for extinction and turbidity measurements, respectively, whereas the axes include a definite angle in measuring devices adapted for nephelometrical measurements. Therefore, measuring devices adapted for extinction, turbidimetrical and nephelometrical measurements are provided with different mostly exchangeable light concentrating optical systems. It is self-understood that the use of such exchangeable optical systems involves high expenditures for cost and material.

It is a further disadvantage of the known technical solutions that the aperture of the optical systems capturing the stray radiation is comparatively low and is not suitable for capturing the stray radiation which is only slightly inclined relative to the direction of the excitation light.

Since in this direction a particularly intensive stray radiation is lost for the analysis operation it is substantially not feasible to reduce the layer thickness and/or the volume of the sample material to be analyzed with the known arrangements.

OBJECTS OF THE INVENTION

It is an object of the present invention to obviate the above disadvantages.

It is a further object of the present invention to provide an optical arrangement which permits an increase of intensity with absorption, fluorescence nephelometrical and turbidimetrical measurements and/or a reduction of the excitation radiation contained in the fluorescence radiation or stray radiation impinging upon the radiation detector.

It is still a further object of the present invention to provide an arrangement of optical components having a common optical axis and which is suitable for absorption measurements as well as for fluorescence, extinction, nephelometrical and turbidimetrical measurements, and which in the event of fluorescence measurement, exploits the excitation radiation which is split from the fluorescence radiation after excitation, again for a fluorescence excitation.

It is still a further object of the present invention to provide an optical arrangement in which the aperture of the stray radiation capturing system is increased so that also those portions of the stray radiation are captured which are only slightly inclined relative to the excitation radiation.

SUMMARY OF THE INVENTION

In accordance with the present invention, an optical arrangement is provided for photometric analysis measuring devices, particularly for use in fluorescence or absorption, extinction nephelometrical or turbidimetrical measurements in which a monochromatic radiation is directed upon a sample to be analyzed and the resulting radiation incorporating the measuring magnitude is directed upon a detector, characterized in that an optical imaging system is arranged between the sample to be analyzed and the detector. Said optical imaging system has an aperture greater than the opening angle of the bundle of monochromatic radiation. Adjacent to said optical imaging system an optical member is provided adapted for insertion into and removal from out of the path of radiation. Said optical member, when inserted, serves to blank out the radiation portions which do not contain measuring information. Advantageously the optical member is an imaging reflector when used in fluorescence measurements, the reflecting face of which is in opposition to the sample to be analyzed. Said imaging reflector images the sample to be analyzed into itself.

When a long wavelength threshold is set for the monochromatic radiation used to excite the sample to fluorescence, it is advantageous when the material of the optical imaging system absorbs the monochromatic radiation. In the event of nephelometrical measurements an absorbing member is inserted into the path of radiation adjacent the optical imaging system. Said absorbing member which is adapted to the aperture of the bundle of monochromatic radiation covers the central range of the optical imaging system and absorbs the light bundle passing the sample material and being weakened by the same. In the event of extinction or turbidimetrical measurements an absorbing member is provided for insertion into the path of radiation adjacent the optical imaging system. Said absorbing member has a transmissive range for the radiation having passed the sample material and being weakened by the latter. Said absorbing member retains the stray radiation. In a further advantageous solution, a deviating member is associated with the optical imaging system, which the former deviates the radiation being weakened by the passage through the sample material, and directs it for being further processed or annihilated. Alternatively, the deviating member deviates the stray radiation for further processing.

It is also an advantage to provide an opening in the optical imaging system which passes the radiation after having penetrated the sample material, for further processing or for being annihilated and to incline the axis of the optical imaging system relative to that of the bundle of monochromatic radiation. By virtue of the invention the excitation radiation is separated from the fluorescence radiation by a simple blanking out operation, apart from separating the portions of stray radiation and of the radiation weakened by passage through the sample to a high degree. Due to this separation which is performed in or in the vicinity of the optical imaging system, also the stray radiation which is slightly inclined relative to the radiation directly passing the sample contributes to the measuring operation, in the event of nephelometric measurements. Since the stray effect depends on the layer thickness and, hence, the stray radiation is proportional to the layer thickness of the sample within certain limits, it is feasible, by virtue of the invention and in particular by the kind of the measuring operation to reduce the thickness of a sample to be analyzed.

This is also true for a fluorescence measurement due to the excitation radiation being twice exploited. Hence, the solution according to the invention is particularly suited for thin layers, for example, when the samples to be analyzed are arranged in an areal distribution in plate-shaped cells.

BRIEF FIGURE DESCRIPTION

In order that the invention may be more readily understood reference is made to the accompanying drawings which illustrate diagrammatically and by way of example four embodiments thereof and where FIG. 1 is a schematic view of an optical arrangement for photometrical measurements including a removable concave reflector, FIG. 2 is a schematic view of an optical arrangement for photometric measurements including a centrally disposed absorbing member, FIG. 3 is a schematic view of an optical arrangement for photometric measurements with an annular absorption member, and FIG. 4 is a schematic view of an optical arrangement for photometric measurements including means for deviating a radiation which directly passes a sample.

DETAILED DISCLOSURE OF THE INVENTION

In FIGS. 1, 2 and 3 a radiation source 1 emits a bundle of radiation 2 which is directed by a first lens 3 through a field aperture 4 upon a monochromator 5. The resulting monochromatic radiation 6 is directed by a second lens 7 upon a sample 9 provided in a sample mount 8. The sample mount 8 is followed in optical alignment to the optical members mentioned hereinbefore by an optical element (18 in FIG. 1), an optical imaging system 10 and a radiation detector 11. The optical element 18 is a concave reflector in FIG. 1 and is removable from out of the bundle of monochromatic radiation 6 indicated by a double arrow A. The optical element 18 serves to retain the portions of the radiation 6 not containing information about the sample to be analyzed. The optical imaging system 10 is constituted of Fresnel lenses and has an aperture greater than that of the bundle of monochromatic radiation 6.

In FIG. 1 the sample material 9 is excited by the monochromatic radiation 6 to emit a fluorescence radiation, the portion of the radiation energy which impinges upon the reflector 18 is reflected back to the sample 9 and thus enhances the fluorescence radiation intensity. The fluorescence radiation which passes by the concave reflector 18 is captured in a comparatively wide spatial angle by the imaging system 10 and is imaged by the latter upon the radiation detector 11. When the concave reflector 18 is removed by displacement in the directions indicated by the double arrow A the entire arrangement operates in absorption measurement. It is self-understood that the wavelength of the excitation radiation has to be matched accordingly.

Furthermore, it is feasible to fabricate the optical imaging system 10 of reflectors rather than lenses or lens combinations.

It is also feasible to non-displaceably install the concave reflector 18 in the imaging system when only fluorescence measurements have to be performed.

It is also feasible, when a long wavelength threshold is set for the excitation radiation, so to select the material of the imaging system 10 that the excitation radiation is entirely absorbed. In this case, the imaging system 10 has the function of a blocking filter in addition to that of ensuring a wide angle of aperture.

In FIGS. 2 and 3 the monochromatic radiation 6 which passes the sample 9 produces a direct radiation portion 12 and a stray radiation portion 13.

While a light stop 14 is provided for nephelometric measurements which absorbs the first radiation portion 12 and transmits the second passing by radiation portion 13 to the detector 11 the insertable member for extinction and turbidimetrical measurements consists in an annular light stop 15 which transmits the first radiation portion 12 and stops the second stray radiation portion 13.

It is feasible to replace the light stops 14 and 15 by any suitable filter which can be inserted subsequently to the optical imaging system 10 or, when the latter consists of a lens combination, within the same.

In FIG. 4 an alternative embodiment is shown in which the first radiation portion 12 is deviated by a deviating reflector 16 to impinge upon a second detector 17.

This solution also permits all kinds of measurements mentioned hereinbefore the detector 11 receiving the (second) stray radiation portion 13 and the detector 17 the first radiation portion 12.

It is also feasible to embody the deviating reflector in such a manner that the (second) stray radiation portion 13 is deviated and the first radiation portion 12 is detected by the detector 11.

The invention is not restricted to the above embodiments.

It is also feasible to embody the central range of the imaging system 10 permanently opaque, when nephelometric measurements are concerned only.

It is also feasible to provide the imaging system 10 with an opening for distinctly separating the first radiation portion 12 from the (second) stray radiation portion 13. The first radiation portion 12 is then further processed or annihilated. Additionally an axis X—X of the optical imaging system 10 can be inclined relative to an optical axis $X_1$—$X_1$ of the monochromatic radiation 6.

I claim:

1. An optical arrangement in a photometrical measuring device for analyzing a sample material, comprising
    a light emitting system for emitting a bundle of monochromatic radiation to propagate along an optical axis, said light emitting system having a field aperture for said monochromatic radiation,
    a lens,
    a sample mount for mounting a material to be analyzed,
    an optical imaging system,
    a detector means,
    said lens, said sample mount, said optical imaging system and said detector means being sequentially arranged in that order along said optical axis in mutual optical alignment,
    said optical imaging system having an aperture greater than that of the field aperture,
    said monochromatic radiation being focused onto a sample on said sample mount for producing a sample material radiation,
    said sample material radiation being composed of a first radiation portion containing measuring information of said sample material, and of a second radiation portion not containing measuring information,
    said first radiation portion being imaged through said optical imaging system onto said detector means for evaluation, and
    an optical member arranged adjacent to said optical imaging system along said optical axis, said optical member being removable from said optical arrangement in a direction at right angles to said optical axis, said optical member covering a portion of said optical imaging system.

2. An optical arrangement as claimed in claim 1, wherein said optical member comprises means for retaining said second radiation portion.

3. An optical arrangement as claimed in claim 2, wherein for fluorescence excitation, said optical member comprising an imaging reflector having its reflecting face directed toward said sample material to be analyzed and positioned to image said second radiation portion onto said sample material.

4. An optical arrangement as claimed in claim 3, wherein said optical imaging system comprises an absorbing material for absorbing said monochromatic radiation, when a long wave-length threshold is set for the monochromatic radiation employed for fluorescence excitation.

5. An optical arrangement as claimed in claim 2, for nephelometric measurements, wherein said optical member covers a central portion of said optical imaging system, and is adapted to said field aperture, and wherein said second radiation portion is a radiation which directly passes said sample material and is weakened by the latter, said optical member being absorbing for said second radiation portion.

6. An optical arrangement as claimed in claim 2, for extinction sand turbidimetrical measurements, wherein said first radiation portion is a radiation weakened by passing said sample material, and said second radiation portion is stray radiation, said optical member being adapted to absorb said stray radiation and having a transmissive range for said first radiation portion.

7. An optical arrangement as claimed in claim 1, wherein said optical member is arranged between said optical imaging system and said detector along said optical axis,
    said optical member having a reflecting face facing said optical imaging system and inclined relative to said optical axis,
    said optical member serving to deviate said first radiation portion and said second radiation portion, respectively.

8. An optical arrangement as claimed in claim 7, wherein a further detector is provided remote from said detector means in optical alignment with said optical member, for evaluating said first radiation portion.

9. The optical arrangement of claim 1 wherein said aperture of said optical imaging system is substantially continuous throughout the first region adapted to the field aperture as well as a region surrounding and adjoining said first region.

10. The optical arrangement of claim 9 wherein said aperture comprises a Fresnel lens.

* * * * *